United States Patent [19]

Siczek et al.

[11] Patent Number: 5,050,204
[45] Date of Patent: Sep. 17, 1991

[54] C-ARM DIAGNOSTIC EQUIPMENT

[76] Inventors: Bernard W. Siczek; Aldona A. Siczek, both of 1252 Chinook Way, Boulder, Colo. 80303

[21] Appl. No.: 353,359

[22] Filed: May 4, 1989

[51] Int. Cl.⁵ .............................................. H05G 1/02
[52] U.S. Cl. ..................................... 378/197; 378/196
[58] Field of Search ............... 378/195, 196, 197, 198, 378/193

[56] References Cited

U.S. PATENT DOCUMENTS

| | | | |
|---|---|---|---|
| 3,281,598 | 10/1966 | Hollstein | 378/189 |
| 3,892,967 | 7/1975 | Grady | 378/27 |
| 4,150,297 | 4/1979 | Borggren | 378/20 |
| 4,334,155 | 6/1982 | Gieschen | 378/196 |
| 4,358,856 | 11/1982 | Stivender et al. | 378/197 |
| 4,363,128 | 12/1982 | Grady et al. | 378/181 |
| 4,365,343 | 12/1982 | Grady et al. | 378/197 |

FOREIGN PATENT DOCUMENTS 122849 10/1984 European Pat. Off. ............ 378/193

Primary Examiner—Graig E. Church

[57] ABSTRACT

A C-arm diagnostic equipment is disclosed, which equipment provided counterbalanced variable distance between an image source and an image receptor; an increased range of orbital rotation of the C-arm accomplished by a novel arc-in-the arc structure, which structure is counterbalanced for effective control of the orbital rotation; a suspension means with a counterbalanced means for the C-arm to be used as a ceiling suspended C-arm diagnostic equipment, which suspension means are moveably mounted on ceiling rails laterally displaced from, and not extending over, a patient positioned on an examination table and are linearly displaceable along these rails in a direction generally parallel to the lengthwise axis of the examination table.

9 Claims, 3 Drawing Sheets

C-ARM DIAGNOSTIC EQUIPMENT

FIELD OF INVENTION

This invention relates to a C-arm X-ray diagnostic equipment and also to a ceiling suspended C-arm for use in diagnostic examinations and medical treatments.

BACKGROUND OF INVENTION

The use of a C-arm diagnostic equipment in diagnostic examinations and surgical procedures is well known, and such C-arms heretofore have been controlled utilizing various devices and constructions for effecting needed movements.

Improvements in C-arms, however, deemed to be useful and/or needed in some applications. In particular, now known C-arms have failed to provide a sufficient range of orbital movement of the C-arm and a counterbalanced variable distance between an image source and an image receptor, have ceiling rails directly above a patient undergoing a treatment and hence precluding complete sterilization of this zone.

SUMMARY OF INVENTION

This invention provides an improved C-arm apparatus for use in diagnostic and/or medical procedures and which enables substantially sufficient range of orbital displacement of the C-arm (with respect to the curvature of the C-arm) and provides a counterbalanced variable distance between the image source and the image receptor, and further, allows to moveably mount the C-arm on the ceiling rails laterally displaced from, and not extending over, the patient being treated.

It is therefore an object of this invention to provide an improved C-arm useful in diagnostic and surgical procedures.

It is another object of this invention to provide an improved C-arm which C-arm has an adequate orbital rotation of the C-arm and yet allows for varying the distance between the image source and image receptor.

It is still another object of this invention to provide an improved C-arm which has all the movements counterbalanced for effective use.

It is still another object of this invention to provide an improved ceiling suspended C-arm which C-arm is moveably mounted on the ceiling rails laterally displaced from, and not extending over, a patient undergoing the treatment and, thus, facilitating maintaining sterile condition and parking the C-arm away when not in use.

DETAILED DESCRIPTION OF THE PRESENTLY PREFERRED EMBODIMENT

Figure 1:
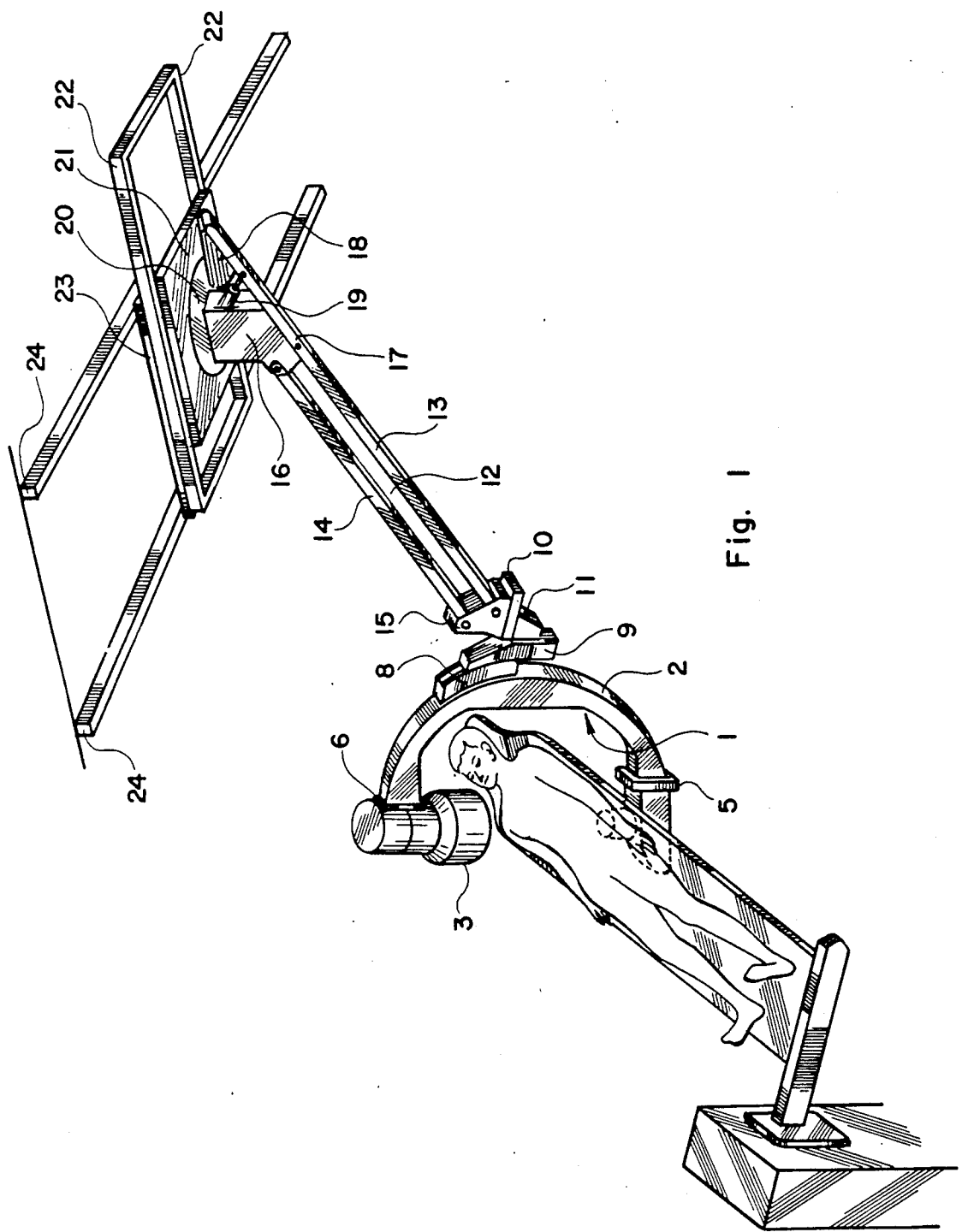
FIG. 1 is an isometric view of the C-arm diagnostic equipment according to the present invention.

The description of this invention is illustrated in relation to a ceiling suspended C-arm diagnostic equipment. A C-arm diagnostic equipment according to this invention is best known by the isometric drawing of FIG. 1, augmented by the side view of FIG. 2.

As shown, C-arm diagnostic equipment comprises:

(1) a C-arm structure 1 being an arc structure 2 with an image source such as an X-ray tube 4 (with an X-ray 7 collimator disposed on the window of said tube) and an image receptor, such as an image intensifier 3 (as shown) or a film cassette or the like, moveably mounted on opposite ends thereof by means of slides 5, 6 respectively, and connected with an actuating means 50 (FIG. 3) for varying the distance therebetween as brought out more fully hereinafter;

(2) an arc-in-the arc structure being an arc member 8 moveably mounted on a second arc member 9 and having C-arm structure 1 moveably mounted thereon for the orbital displacement of the C-arm with respect to the curvature of the C-arm between slides 5 and 6, and also said arc member 8 (and hence the C-arm) being orbitally displaceable with respect to the curvature of said arc member 8 to increase the range of the orbital displacement of the C-arm;

(3) a horizontal structure 10, which structure has a downwardly extending portion 11, which portion has a second arc member 9 rotatably mounted thereon for the rotation of said second member around the predetermined horizontal axis;

(4) a pantograph structure 12 being a pair of two rods 13 and 14 pivotably joined at opposite ends by means of pairs of plates 15 and 16 to form a parallelogram for vertical displacement of the C-arm; horizontal structure 10 being moveably mounted on plate 15;

(5) a counterbalancing means comprising a lengthwise elongated member 17 being an extension of the lower rod 13 and having a counterweight 18 mounted thereon and a compression spring 19 affixed to member 17 at one end and to plates 16 at the opposite end;

(6) a rotating disc 20 having pair of plates 16 mounted thereon and said disc being mounted on a first frame means 21, which means is moveably mounted on rails 22, which rails are moveably mounted on a second frame means 23, which second frame means is moveably mounted on longitudinal rails 24, which rails are rigidly mounted on a ceiling in the direction generally perpendicular to rails 22 and generally parallel to the lengthwise axis of the examination table.

To counterbalance the weight of the C-arm 1 and the weight of arc member 8 for manual control of the orbital displacement, the outer curvature of arc structure 2 is drawn from a center $O_1$, and the outer curvature of arc member 8 drawn from a center $O_2$ so that the ratio of the distance between these two centers and the radius of the outer curvature of arc structure 2 is equal to the ratio of the weight of arc member 8 and the weight of C-arm 1.

Figure 3:
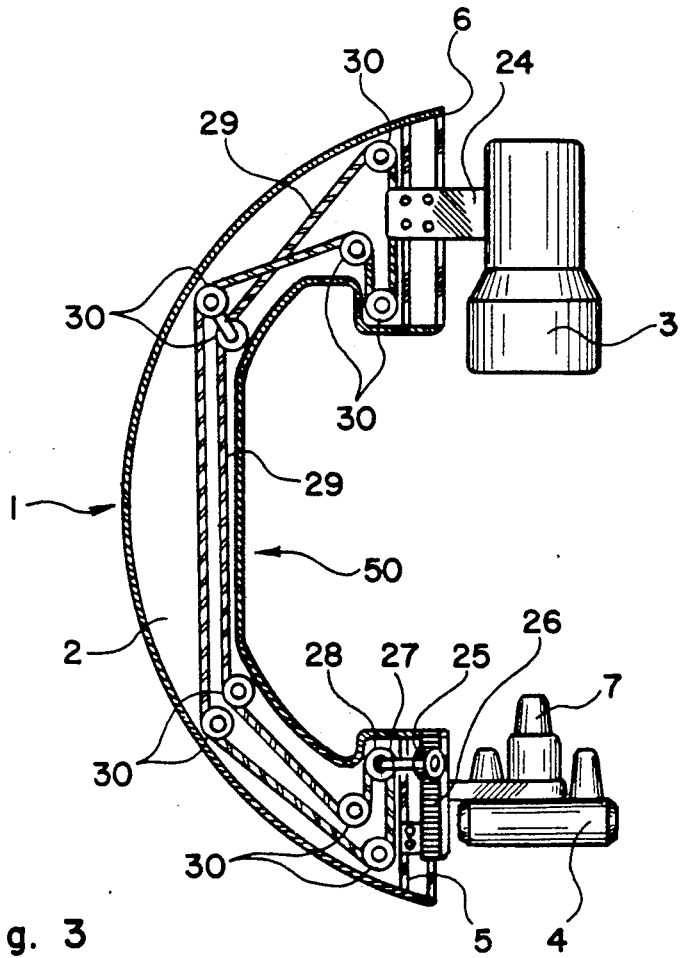
FIG. 3 illustrates the actuating means for varying the distance between the X-ray tube and the image intensifier.

Actuating means 50 for varying the distance between X-ray tube 4 and image intensifier 3 is shown in FIG. 3. Image intensifier 3 is attached to plate 24, which plate is moveably mounted on slide 6 and also connected with a cable 29; X-ray tube 4 is affixed to a rack 26, which rack is moveably mounted on slide 5 and driven by a pinion 25. Pinion 25 is mounted on one end of shaft 27, which shaft has a drum 28 mounted on the opposite end thereof. Cable 29 is affixed to and wound over drum 28 for the length of the displacement of X-ray tube 4 (and hence image intensifier 3), and further, said cable extends over various pulleys 30 so that image intensifier 3 and X-ray tube 4 move in unison toward and away from one another. To counterbalance this movement, a ratio of the pitch diameter of the drum 28 to the pitch diameter of pinion 25 is selected to equal the ratio of the weight of X-ray tube 4 (with collimator 7) to the weight of image intensifier 3 (with plate 24).

Figure 4:
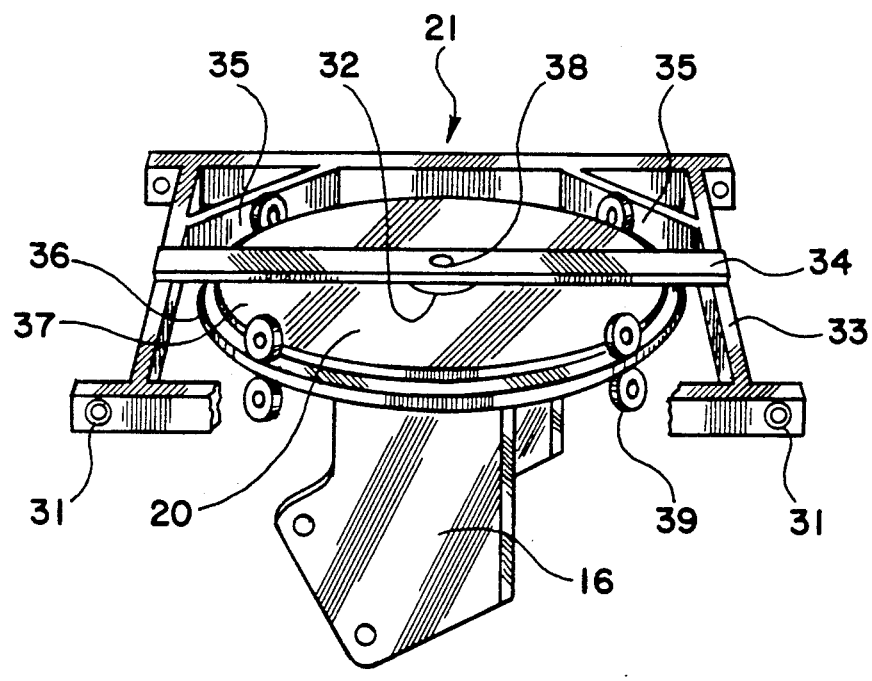
FIG. 4 illustrates the suspension means of the C-arm structure.

FIG. 4 shows rotating disc 20 and first frame means 21, which frame means comprises a frame 33 with a cross member 34 connecting two opposite sides of frame 33 and having four struts 35 (shown two). Frame 33 (and hence the C-arm) moves on four bearings 31 along rails 22. Rotating disc 20 comprises a larger diameter, thinner lower disc 36 (made of hard material) and a smaller diameter upper disc 37 (made of lighter material), which discs are bound together by an adhesive. Disc 37 includes a hub for a bearing 32 which bearing is secured by a pin 38 placed in cross member 34. Disc 20 (and hence the C-arm) rotates between four pairs of bearings 39.

Figure 2:
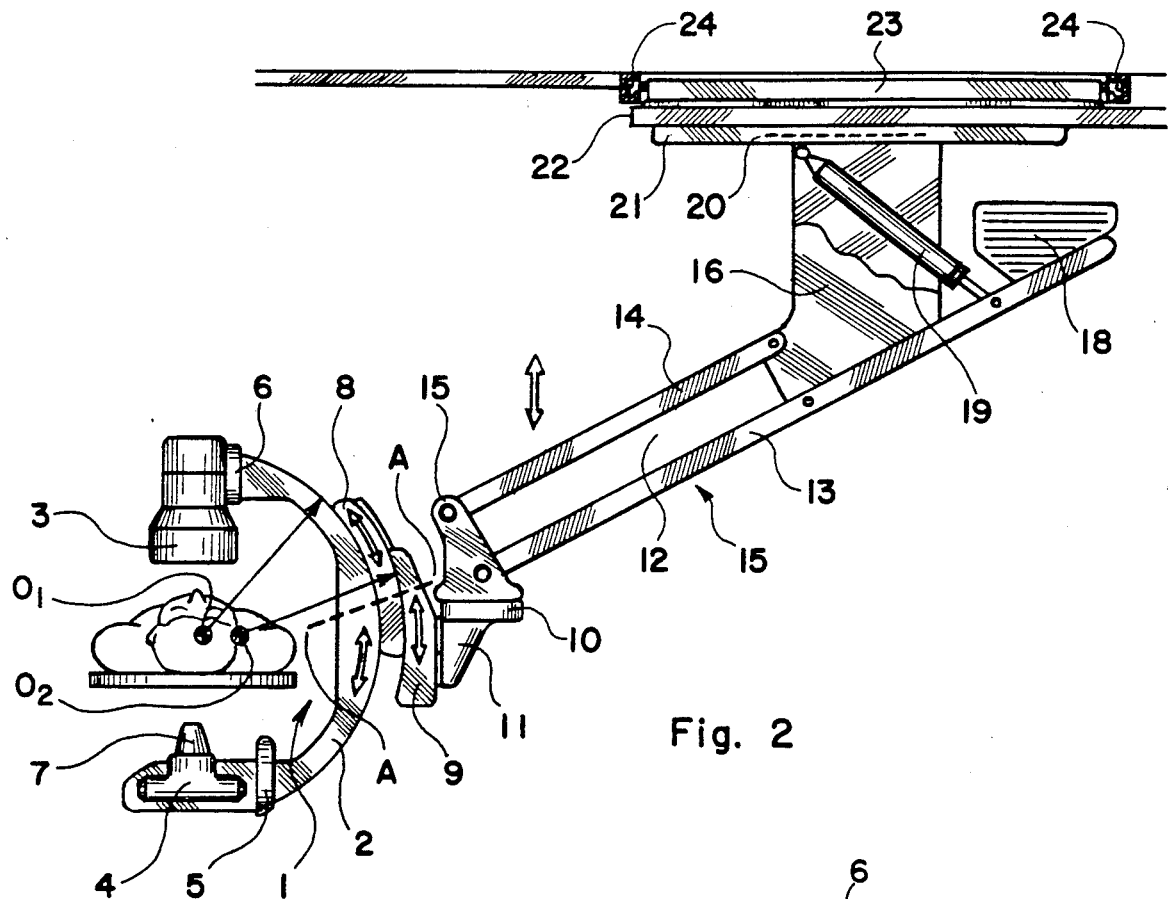
FIG. 2 is a side view of the C-arm.
Figure 5:
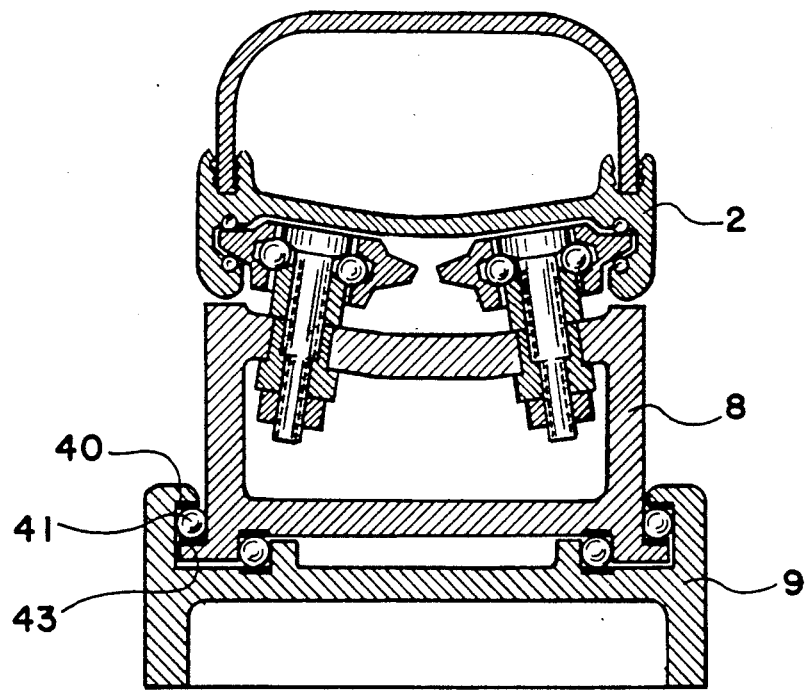
FIG. 5 is a cross section through a line A—A of FIG. 2.

FIG. 5 is a cross section taken through line A—A of FIG. 2 illustrating arc-in-the arc structure (8,9) and arc structure 2 (which structure is discussed in detail in another co-current patent application). Arc member 8 is moveably mounted on arc member 9 by means of inserts 40 and 43 made of a hard material and imbedded in member 8 and member 9 to form channels in the shape of an arc, in which channels balls 41 roll to facilitate orbital displacement of member 8 with respect to member 9.

What is claimed is:

1. A C-arm apparatus being used in diagnostic examinations, said apparatus comprising:
   a support means having a C-arm mounted thereon, which C-arm being an arc structure having an X-ray source (with a rack) X-ray receptor moveably mounted on opposite ends thereof and being connected with an actuating means causing displacement of said X-ray source and said X-ray receptor in unison toward and away from one another, said actuating means including: said rack moveably mounted on said arc structure, a pinion engaging said rack and mounted on a shaft, which shaft has also a drum mounted thereon, and a cable affixed to and wound over said drum for the length of said displacement, said cable extended over various pulleys.

2. The apparatus of claim 1, wherein the ratio of the pitch diameter of said drum and of said pinion is equal to the ratio of the weight of said X-ray source to the weight of said X-ray receptor.

3. A ceiling suspended C-arm apparatus being used in diagnostic examinations, said apparatus comprising a C-arm being an arc structure having an X-ray source and X-ray receptor mounted on opposite ends thereof, said C-arm mounted on a suspension means, said means moveably mounted on a ceiling mounted rail means, wherein said rail means are laterally displaced from, and not extending over, an examination table having a patient positioned thereon.

4. A ceiling suspended C-arm apparatus being used in diagnostic examinations, said apparatus comprises a C-arm being an arc structure having an X-ray source and X-ray receptor mounted on opposite ends thereof, said C-arm mounted on a suspension means, said means mounted on a disc, which disc is rotatably mounted on the ceiling and comprises a larger diameter, thinner lower disc made of hard material and a smaller diameter upper disc made of lighter material, which said discs are joined together with an adhesive, and wherein the edge of said lower disc rotates between pairs of bearings.

5. A C-arm apparatus being used in diagnostic examinations, said apparatus comprising:
   a C-arm being an arc structure having an X-ray source and an X-ray receptor mounted on opposite ends thereof, an arc-in-the arc supporting means, said means being a first arc member, which member has said C-arm moveably mounted thereon, and a second arc member, which second arc member has said first arc member moveably mounted thereon, and said C-arm being orbitally displaceable with respect to the curvature of the C-arm and said first arc member being orbitally displaceable with respect to the curvature of said first arc member.

6. The apparatus of claim 5, wherein said arc structure has an outer curvature drawn from a center $O_1$ and said first arc member has the outer curvature drawn from a center $O_2$ so that the ratio of the distance between said centers to the radius of the outer curvature of said arc structure is equal to the ratio of the weight of said first arc member and the weight of said C-arm.

7. The apparatus of claim 5, wherein said first arc member is moveably mounted on said second arc member by means of inserts made of hard material and imbedded in said first and said second members so that said inserts are channels in the shape of arc, in which channels balls roll to facilitate orbital displacement of said first arc member with respect to said second arc member.

8. A ceiling suspended C-arm apparatus being used in diagnostic examinations, said apparatus comprising:
   a C-arm being an arc structure having an X-ray source and an X-ray receptor mounted on opposite ends thereof, said C-arm mounted on a suspension means mounted on a ceiling, said means being a panthograph structure having two rod members joined to form a parallelogram, a counterbalancing means including a lengthwise elongated member extending from one of said rod members and having a counterweight mounted thereon and a spring affixed at one end to said elongated member and at the opposite end to said panthograph structure.

9. The system of claim 8, wherein said suspension means are mounted on a frame means, which frame means are moveably mounted on a rail means for linear displacement along said rail means, said displacement being in a direction generally parallel to the lengthwise axis of an examination table having a patient positioned thereon.

* * * * *